(12) United States Patent
Simpson et al.

(10) Patent No.: US 11,491,299 B2
(45) Date of Patent: Nov. 8, 2022

(54) DUAL CONVECTION AND CONDUCTION OVEN FOR FLOWER STICK

(71) Applicant: Flat Planet Limited, Kowloon (HK)

(72) Inventors: Michael Lee Simpson, Santa Monica, CA (US); Matthew James Bickerton, Topanga, CA (US)

(*) Notice: Subject to any disclaimer, the term of this patent is extended or adjusted under 35 U.S.C. 154(b) by 54 days.

(21) Appl. No.: 16/945,665

(22) Filed: Jul. 31, 2020

(65) Prior Publication Data

US 2021/0030996 A1 Feb. 4, 2021

Related U.S. Application Data

(60) Provisional application No. 62/836,641, filed on Apr. 20, 2019.

(51) Int. Cl.
| | | |
|---|---|---|
| *A61M 21/00* | (2006.01) | |
| *A24F 40/20* | (2020.01) | |
| *A24F 40/46* | (2020.01) | |
| *H05B 1/02* | (2006.01) | |

(52) U.S. Cl.
CPC .............. *A61M 21/00* (2013.01); *A24F 40/20* (2020.01); *A24F 40/46* (2020.01); *H05B 1/0202* (2013.01); *H05B 1/0252* (2013.01); *A61M 2021/0016* (2013.01); *A61M 2205/3368* (2013.01); *A61M 2205/3653* (2013.01)

(58) Field of Classification Search
CPC .................... A61M 21/00–02; A24F 40/00–95
See application file for complete search history.

(56) References Cited

U.S. PATENT DOCUMENTS

| 7,434,584 | B2 | 10/2008 | Steinberg | |
|---|---|---|---|---|
| 10,334,881 | B1* | 7/2019 | Conley | ................. A24F 40/42 |
| 10,517,331 | B2 | 12/2019 | Atkins | |
| 2011/0061666 | A1 | 3/2011 | Dube | |
| 2014/0041655 | A1* | 2/2014 | Barron | ................. A24F 40/46 |
| | | | | 128/202.21 |
| 2015/0101606 | A1* | 4/2015 | White | ................. A61M 15/00 |
| | | | | 131/194 |
| 2015/0128967 | A1 | 5/2015 | Robinson | |

(Continued)

FOREIGN PATENT DOCUMENTS

WO 2019106102 A1 6/2019

OTHER PUBLICATIONS

ISA/US. International Search Report, PCT/US2021/044095, dated Apr. 13, 2022.

(Continued)

*Primary Examiner* — Thaddeus B Cox
(74) *Attorney, Agent, or Firm* — Benjamin P. Kuo, Esq.

(57) ABSTRACT

A heating oven for use with a heat-not-burn portable heating device for the delivery of vaporized natural consumables, and methods of operating the oven are disclosed. The oven heats a flower stick filled with natural consumables to vaporize volatile compounds for the inhalation and enjoyment of the user. The oven operates by both conduction and convection via knitted wire filters that have high surface area and thermal mass to enable rapid heat transfer and stabilization of temperatures. The oven operates according to one or more temperature profiles for the duration of a heating session.

20 Claims, 13 Drawing Sheets

(56) References Cited

U.S. PATENT DOCUMENTS

| | | | |
|---|---|---|---|
| 2016/0157524 A1* | 6/2016 | Bowen | G01N 33/0027 |
| | | | 702/50 |
| 2016/0262459 A1 | 9/2016 | Monsees | |
| 2017/0027223 A1* | 2/2017 | Eksouzian | A24F 40/60 |
| 2018/0000160 A1* | 1/2018 | Taschner | H05B 3/44 |
| 2018/0092400 A1 | 4/2018 | Sahin | |
| 2018/0146709 A1* | 5/2018 | Bessant | H05B 3/04 |
| 2018/0154103 A1* | 6/2018 | Davis | A61M 16/0066 |
| 2018/0289906 A1* | 10/2018 | Trzecieski | A24F 40/40 |
| 2019/0116875 A1 | 4/2019 | England | |
| 2019/0200677 A1 | 7/2019 | Chong | |
| 2020/0015516 A1 | 1/2020 | Simpson et al. | |

OTHER PUBLICATIONS

ISA/US. Written Opinion of the International Searching Authority, PCT/US2021/044095, dated Apr. 13, 2022.

ISA/US. Notification of Decision on Protest or Delcaration that Protest Considered Not to Have Been Made, dated Mar. 28, 2022.

\* cited by examiner

DUAL CONVECTION AND CONDUCTION OVEN FOR FLOWER STICK

CROSS-REFERENCE TO RELATED APPLICATIONS

This application claims benefit of priority to prior-filed U.S. Applications 62/836,641 titled "Herb Delivery System and Filling Method" and filed Apr. 20, 2019, of which the entire contents thereof are hereby incorporated by reference into the present disclosure.

BACKGROUND OF THE INVENTION

The present invention relates generally to a heating device that heats a disposable flower stick or flower cartridge that facilitates the smokeless delivery of active ingredients and volatile compounds released from a quantity of natural consumables that have been pre-filled in the stick. The heating device is used to vaporize the natural consumables in the cartridge by convective heating of ambient air and by conductive heating of the stick via surface area contact, thereby releasing volatile compounds at specified temperature profiles.

A flower stick (also known as a flower cartridge) dispenses a consistent amount of natural consumables, which comprise ground flower and plant matter. Such a stick may dispense an accurate dosage of natural consumables for predictable and measured enjoyment by the user. A stick containing natural consumables in the form of ground flower or plant matter may allow the extraction and delivery of active ingredients and volatile compounds.

Traditionally, smokers relied on combustion of natural consumables in the form of cigarettes or other assistive devices to inhale the active ingredients. The present invention relies on heat-not-burn technology, wherein instead of burning, mere heating is applied, which raises the temperature of natural consumables above the vaporization temperature of the active ingredients but below combustion temperatures. A stick pre-filled with natural consumables obviates the need to separately load the natural consumables into a heating or burning device by the user, nor is there any requirement to rely on ignition sources.

The fabrication materials of the stick are non-combustible within the normal operating range of the heating device nor at the vaporization temperatures of the active ingredients, such that the stick and the natural consumables may be heated to various temperatures for the extraction of desired chemicals by the convective transfer of heated air and conduction with the oven walls, not combustion. The "smokeless" feature of a stick helps mitigate the deleterious health effects associated with smoking.

Patent disclosures pertaining to the construction and filling of the sticks/cartridges may be found in U.S. application Ser. No. 16/509,469 titled "Flower Cartridge Crimping and Filling for Herb Delivery," filed on Jul. 11, 2019; and International Application No. PCT/US2019/41499 titled "Flower Cartridge for Herb Delivery," filed on Jul. 11, 2019, of which the entire contents thereof are hereby incorporated by reference into the present disclosure.

Accordingly, there is a need in the art for an improved oven as an integral element of a novel portable heating device for the delivery of vaporized natural consumables, which operates by both convection of heated air and conduction by contact of the stick and oven walls.

BRIEF SUMMARY OF THE INVENTION

The present invention makes use of a dual convection-conduction oven. By way of illustration, a conduction-only vaporizer draws cool air into the oven when the user draws, cooling the contents and giving a reduced output and disappointing "cold" experience on voluminous draws. A convection-only vaporizer, on the other hand, need to raise the temperature on each draw by such a significant amount that some parts of the stick may reach or exceed charring temperatures before the natural consumables farthest from the heat source are activated. Using both convection and conduction allows the vaporizer to maintain the contents at an optimal temperature between user draws, and preserves flexibility when air is actively circulated.

In addition, features such as the use of the knitted wire filters with properties of high surface area, high thermal mass, high thermal conductivity, and particular construction aspects of the knitted wire filters themselves, that controlled heating of the flower stick can be achieved.

According to an aspect of the present invention, a heating oven is situated within a portable heating device, that when coupled with a flower stick containing natural consumables, is able to deliver vaporized substances at desired dosages with preset temperature profiles.

The heating oven is operable by electrical signaling, and turns on when current is applied to a heater coil located near the bottom of the oven. Electrical signaling occurs via the triggering of one or more stick switches located near the top of the oven. When the user inserts a stick to begin the heating session, the stick is guided mechanically via the stick guide as it is inserted into the oven. Two stick switches embedded in their respective switch holders, which are in turn embedded in the guide, are trigged as the stick pushes against them, which turns on the heater coil.

The heater coil functions by transferring heat by convection to air currents moving past it, and also warms by conduction a main oven tube, a second oven tube, a first knitted wire filter, and a second knitted wire filter. An insulation blanket is concentrically positioned outside of the oven tubes to help retain heat. Temperature sensors are placed between the two knitted wire filters, and also attached to the main oven tube.

An inserted stick is guided mechanically down the main oven tube until it comes to rest against the second knitted wire filter and is properly positioned for the duration of the heating session. Heat from the main oven tube preheats the stick and the natural consumables within via conduction. An oven top gasket creates an interference fit against the stick above the main oven tube and the main oven tube forms a close fit with the inserted stick.

The stick serves as a mouthpiece from which the user inhales vaporized consumables. As the user draws from the stick, negative pressure is created, and ambient air enters the oven in the space between the stick and the stick guide and flows out of the guide via preformed channels that lead to one or more air tubes situated lengthwise proximate to the insulation blanket.

Air travels down the tubes toward the bottom of the oven until it enters a base assembly, where it enters a cavity directly below the heater coil. Negative pressure draws the air upward into the coils where heat transfer by convection occurs. Additional heat transfer occurs as the air flows upward into the first knitted wire filter and the second knitted wire filter. These filters are made of thin knitted or woven wires compressed into cylindrical shapes, and when placed in the path of air, their high surface areas are adapted to condition the air to an appropriate temperature as it enters the stick directly above the second knitted wire filter.

In an exemplary embodiment, the heating oven would be adapted to raise and lower the temperature of the stick and the contents within according to an ideal temperature profile. Such a profile would require the oven to raise and maintain the temperature of the stick to approximately 195° C., which is a temperature above the vaporization temperature of a majority of active ingredients but below temperatures that would cause charring or burning. Toward the end of the session, the profile would raise the stick temperature to approximately 220° C., releasing a second set of volatile compounds.

An ideal temperature profile cannot always be maintained depending on environmental and user conditions. In another embodiment, a desired temperature profile would require the heating element to raise the oven temperature profile to between 200-300° C. and thereafter gradually lower input power to account for changes within the natural consumables as the session progresses. Toward the end, the temperature profile requires the oven to raise the temperature above 200° C. to facilitate the release of the second set of volatile compounds.

The power applied to the oven, in actual use, only roughly correspond to the oven temperature profile. Many factors can affect the actual temperature of the oven and thus the actual temperature of the stick. For example, heating must be increased significantly when the user draws from the device and circulates a large amount of ambient air into the oven in a short time. The oven temperature sensors detect these fluctuations and is able to vary the amount of power into the device responsive to conditions. In yet another embodiment, the temperature of the oven warms to a certain value and increases with each draw, which minimizes the time in which the stick temperature exceeds 200° C.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The drawings referred to herein are for the purpose of illustrating the preferred embodiments of the present invention and not for the purpose of limiting the same.

Figure 1A:
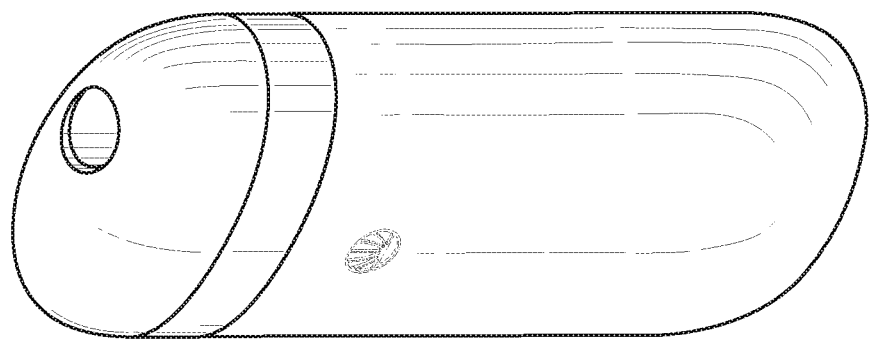
FIG. 1A is a perspective view of the portable heating device.
Figure 1A:
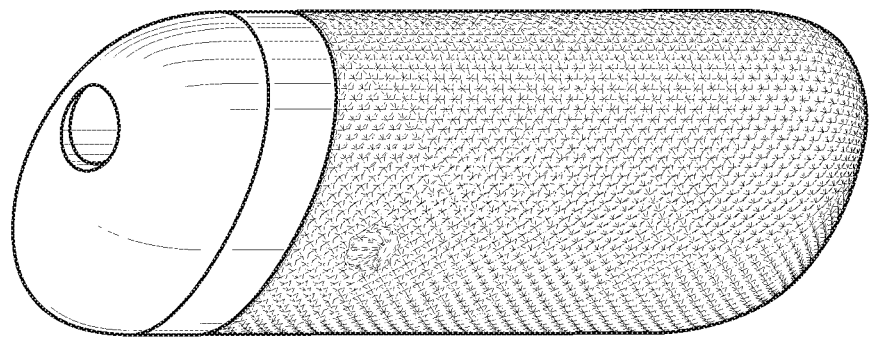
Figure 1B:
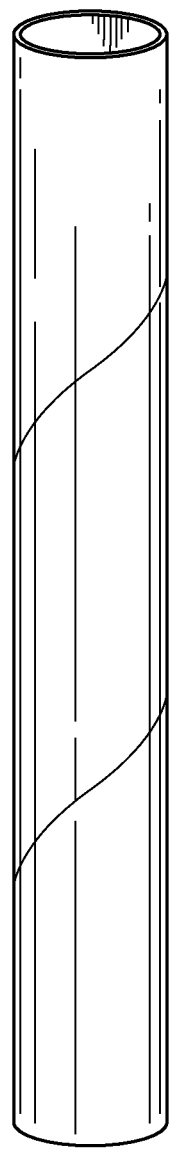
FIG. 1B is a perspective view of the flower stick.
Figure 1C:
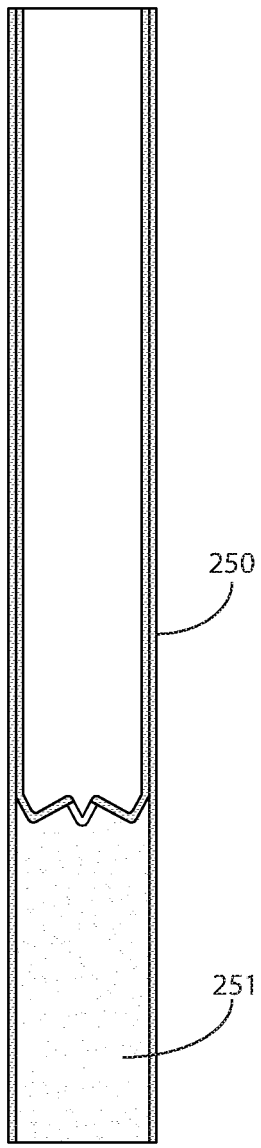
FIG. 1C is a sectional view of the flower stick.

FIG. 1A illustrates an embodiment of the portable heating device adapted for use with a flower stick 250 by insertion via the hole near the top of the device, shown in FIG. 1B. FIG. 1C is a sectional of the flower stick with the insertion end facing down. The insertion end is filled with natural consumables 251, while the mouthpiece end is empty. The stick is disclosed in detail in U.S. application Ser. No. 16/509,469 titled "Flower Cartridge Crimping and Filling for Herb Delivery."

Figure 2A:
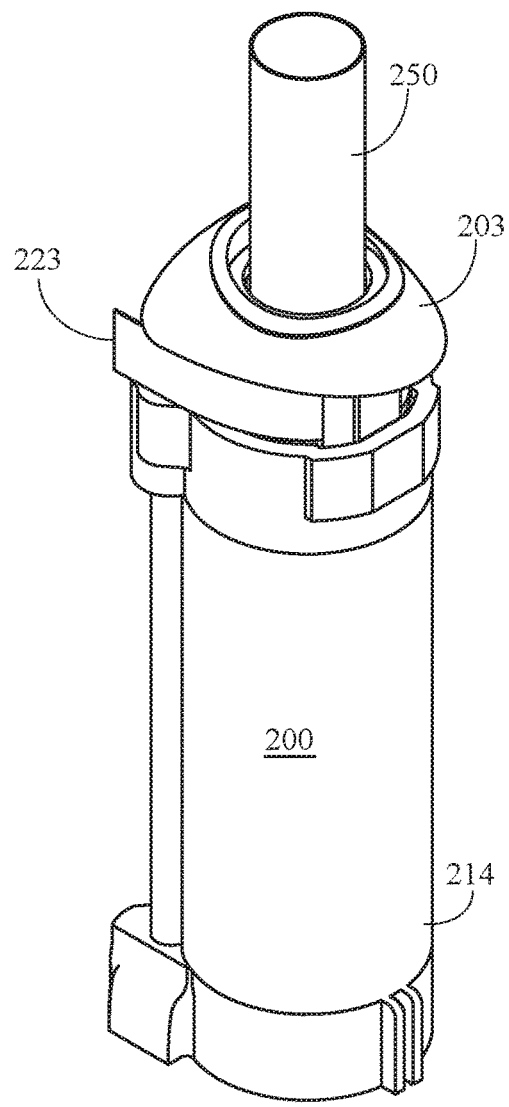
FIG. 2A is a perspective view of the heating oven and the flower stick.

FIG. 2A illustrates an embodiment of the heating oven 200 with a flower stick 250. A stick guide 203 physically aligns the stick for proper positioning within the oven and a PCB strip 223 necessitates proper electrical connections and helps create an airtight seal. An insulation blanket 214 forms an outer shell to help retain heat and is visible in this figure as the outer "wall" of the oven.

Figure 2B:
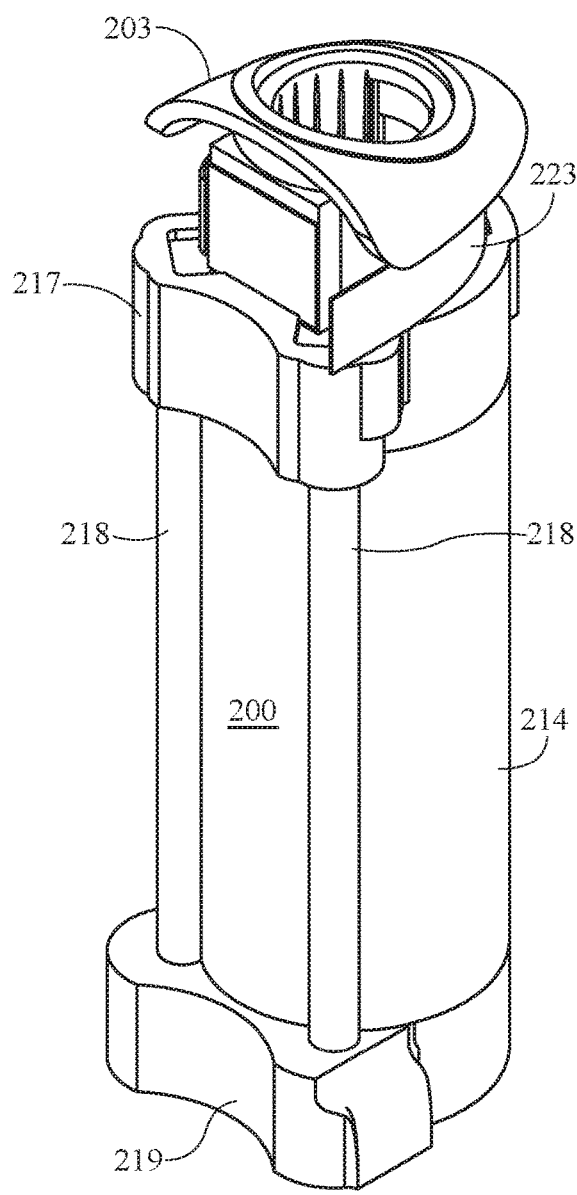
FIG. 2B is a perspective view of the heating oven rotated 90 degrees.

FIG. 2B is a rotated view of the heating oven to show additional elements, among them an oven top gasket 217, air tubes 218, and base assembly 219.

Figure 2C:
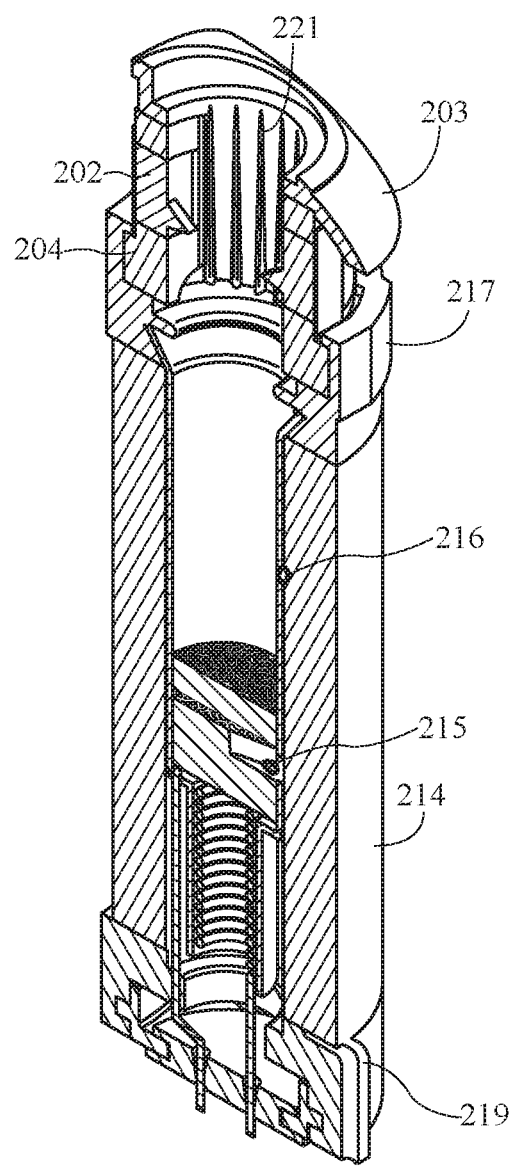
FIG. 2C is a sectional view of the heating oven.

FIG. 2C is a sectional view of the heating oven without a stick and shows the positioning of stick guide 203 and spines 221 positioned within the inner cavity portion of the guide. In the presence of a stick, the spines create spacing between the stick and the stick guide and allows air to circulate. Also illustrated are oven top gasket 217 and base assembly 219. In addition, one or more stick switches 202 are embedded in their respective switch holders 204. The switches are shown in their "off" position where the mechanical switches protrude into the cavity in the absence of a stick.

Figure 2D:
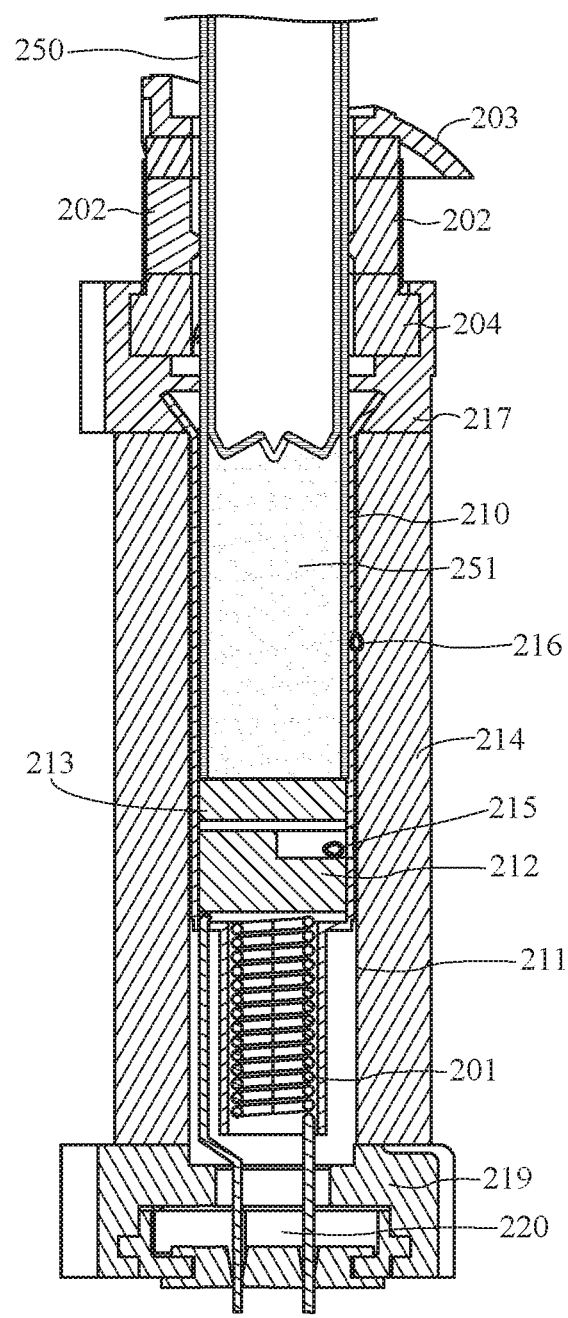
FIG. 2D is a sectional view of the heating oven with the flower stick inserted.

FIG. 2D is a sectional view of the heating oven with a flower stick 250 inserted. Natural consumables 251 rests in the stick, with its approximate fill level flush with the oven top gasket. The stick has reached its proper position when it has come to rest against the second knitted wire filter 213. The fill level is configured such that the portion of the stick that forms a close fit with main oven tube 210 is also the portion filled with natural consumables, achieving optimal heating of the consumables by conduction. The oven top gasket 217 may be made of silicone, and creates an interference fit against the stick above the main oven tube and prevents air from moving past the gasket when the stick is inserted.

The heating oven is operable by electrical signaling, and begins heating when current is applied to a heater coil 201. Electrical signaling occurs via the triggering of one or more stick switches 202. When the user inserts a stick to begin the heating session, as presently illustrated in FIG. 2D, the stick is guided mechanically via the stick guide 203 as it is inserted into the oven. The stick switches, embedded in their respective switch holders 204 are triggered as the stick pushes against them and signals for the heater coil to be energized. The switches are shown in their retracted, or "on" position. The signal is transferred to control circuitry via the PCB strip, which wraps around the stick guide and is soldered to the stick switches. The PCB strip also serves to reduce air leakage around the stick guide.

The heater coil functions by transferring heat by convection to air currents moving past it, and also warms by conduction a main oven tube 210, a second oven tube 211, a first knitted wire filter 212, and a second knitted wire filter 213. The main oven tube comprises two segments, one with a larger diameter adapted for fitting the flower stick, and another with a smaller diameter configured to be slightly larger than the diameter of the heater coil, concentrically placed in close proximity to the coil. The main oven tube is therefore adapted to absorb significant portions of heat energy from the coil and conducts it to the rest of the oven tube and to the knitted wire filters, which in turn warms the flower stick and natural consumables.

Heat may also be transferred via convection of hot air between any of these parts to help distribute thermal energy. The insulation blanket 214 is concentrically positioned outside of the oven tubes to help retain heat. A first temperature sensor 215 is placed in the preformed notch of the first knitted wire filter and detects the temperature close to the heating elements. A second temperature sensor 216 is attached to the main oven tube and detects the temperature close to the flower stick. The temperature sensors should be rated to at least 300° C.

In other embodiments, the oven can operate without a second temperature sensor, and the heater coil may be substituted for any suitable heating element.

Figure 2E:
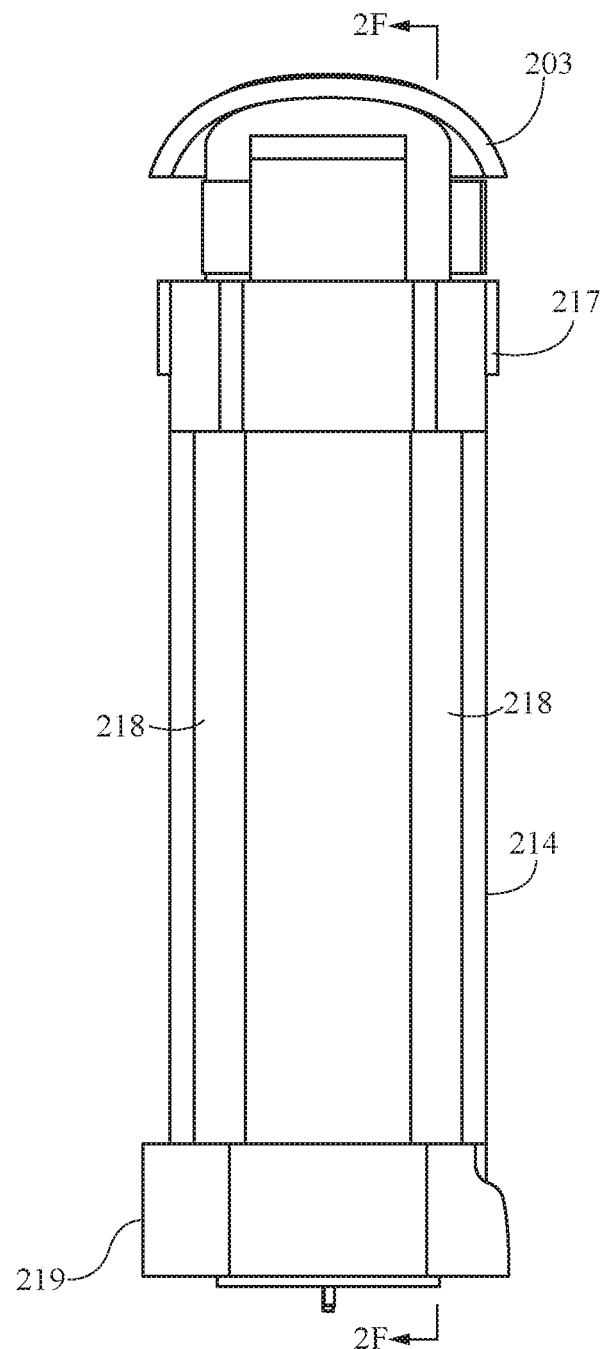
FIG. 2E is an elevational view of the heating oven with the air tubes visible.
Figure 2F:
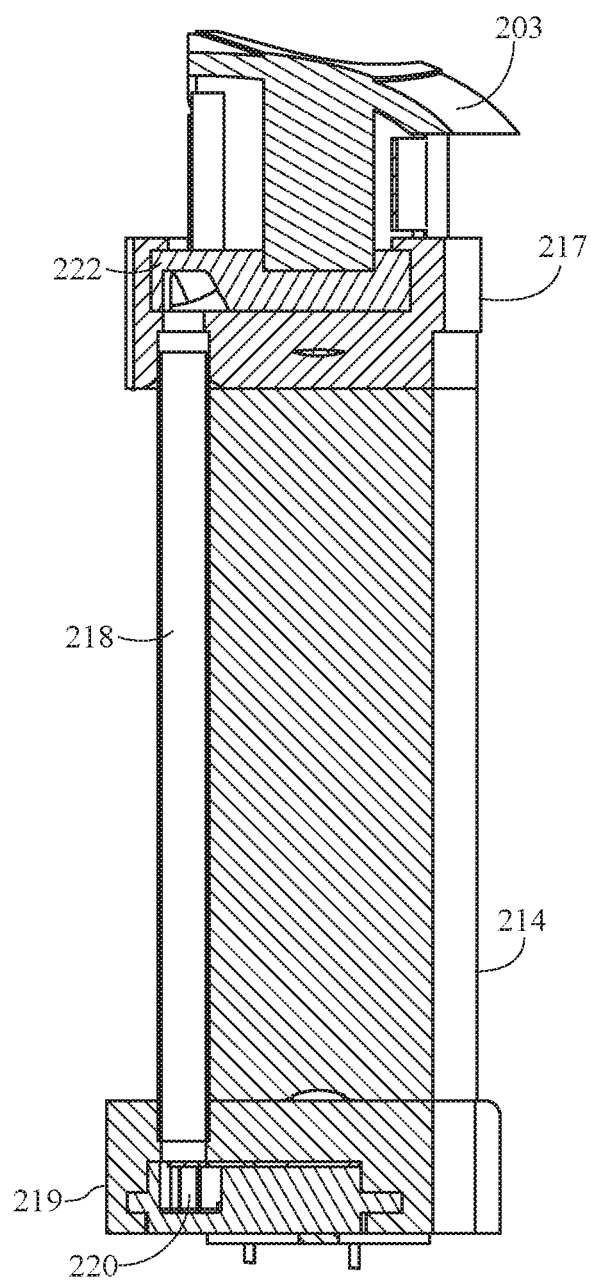
FIG. 2F is a sectional view of an air tube within the heating oven.

FIGS. 2E and 2F show the heating oven with the air tubes facing the viewer, and a sectional showing the path of ambient air as it travels through the device. The stick serves as a mouthpiece from which the user inhales vaporized consumables. As the user draws from the stick, negative pressure is created, and ambient air enters the oven in the space between the stick and the stick guide 203. Air flows downward from the stick guide into preformed channels 222 within oven top gasket 217 that lead to air tubes 218, where it travels down the tubes toward the bottom of the oven until it enters a cavity 220 within base assembly 219, directly below the heater coil.

Returning to FIG. 2D, negative pressure draws the air pooled in cavity 220 upward into the coil where heat transfer by convection occurs. At this point in the session, the knitted wire filters have been preheated conductively, heat having passed directly along the bonded components. Additional heat transfer occurs as hot air flows upward into the first knitted wire filter and the second knitted wire filter and reaches an appropriate temperature as it flows into the stick and heats the natural consumables within.

Figure 2G:
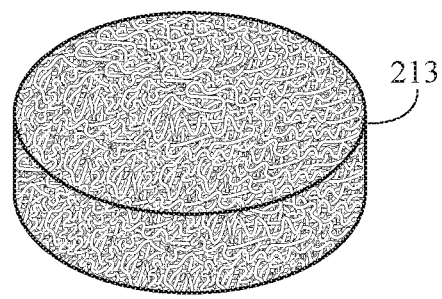
FIG. 2G is an exploded view of the major heating oven components.
Figure 2H:
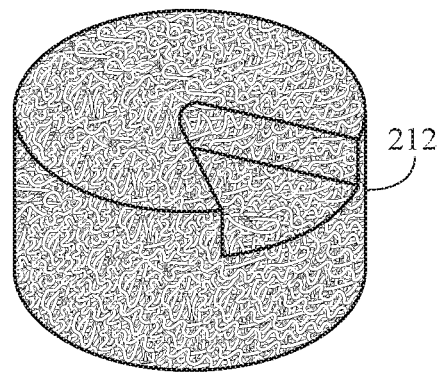
FIG. 2H is a detailed view of the second knitted wire filter.

The knitted wire filters are shown in FIGS. 2G and 2H. They are made from knitted or woven metal wires that are compressed into a cylindrical shape and adapted to fit the inside of the oven tubes. These characteristics enable the filters to have high surface area, thermal mass, and conductivity. They are excellent heat conductors, and also serve as heatsinks/heat buffers to help even out temperature fluctuations caused by the user's drawing from the stick, which may move large amounts of air intermittently. The selection of materials in construction of the components primarily involved in convectional heating means their temperature can be maintained at a higher temperature than the conductive components.

In an exemplary embodiment, the first knitted wire filter 212 may contain a suitable slot, indentation, or notch to facilitate positioning of the first temperature sensor 215. This filter is positioned nearest to the heater coil, is made of aluminum, which has a higher thermal conductivity and a lower thermal mass than steel, which means it readily gives up heat to circulating air, heats and cools quickly, and is more responsive at heat transfer.

The second knitted wire filter 213, positioned nearest to the stick, is made of stainless steel, which has a lower thermal conductivity and higher thermal mass than aluminum, which serves to retain heat and to regulate the temperature of the air current and the oven tube above it.

In another exemplary embodiment, any other metal with suitable thermal properties, low toxicity, and non-corrosive properties, such as brass or copper, may be used. The first knitted wire filter has an approximate density of 1.11 g/cm³. The second knitted wire filter has an approximate density of 2.5 g/cm³. Exemplary wire thicknesses can range from 0.05-0.1 mm; wire thickness would determine the effective surface area of metal available for heat exchange.

The first knitted wire filter is capable of transferring large amounts of heat to efficiently raise the temperature of large volumes of air as it passes through. In contrast, the second knitted wire filter requires more energy to change its temperature and helps regulate fluctuations as well as serve as a temperature barrier of the oven tubes containing the stick. These filters are adapted to condition the air to an appropriate temperature as it enters the stick directly above the second knitted wire filter.

Figure 2J:
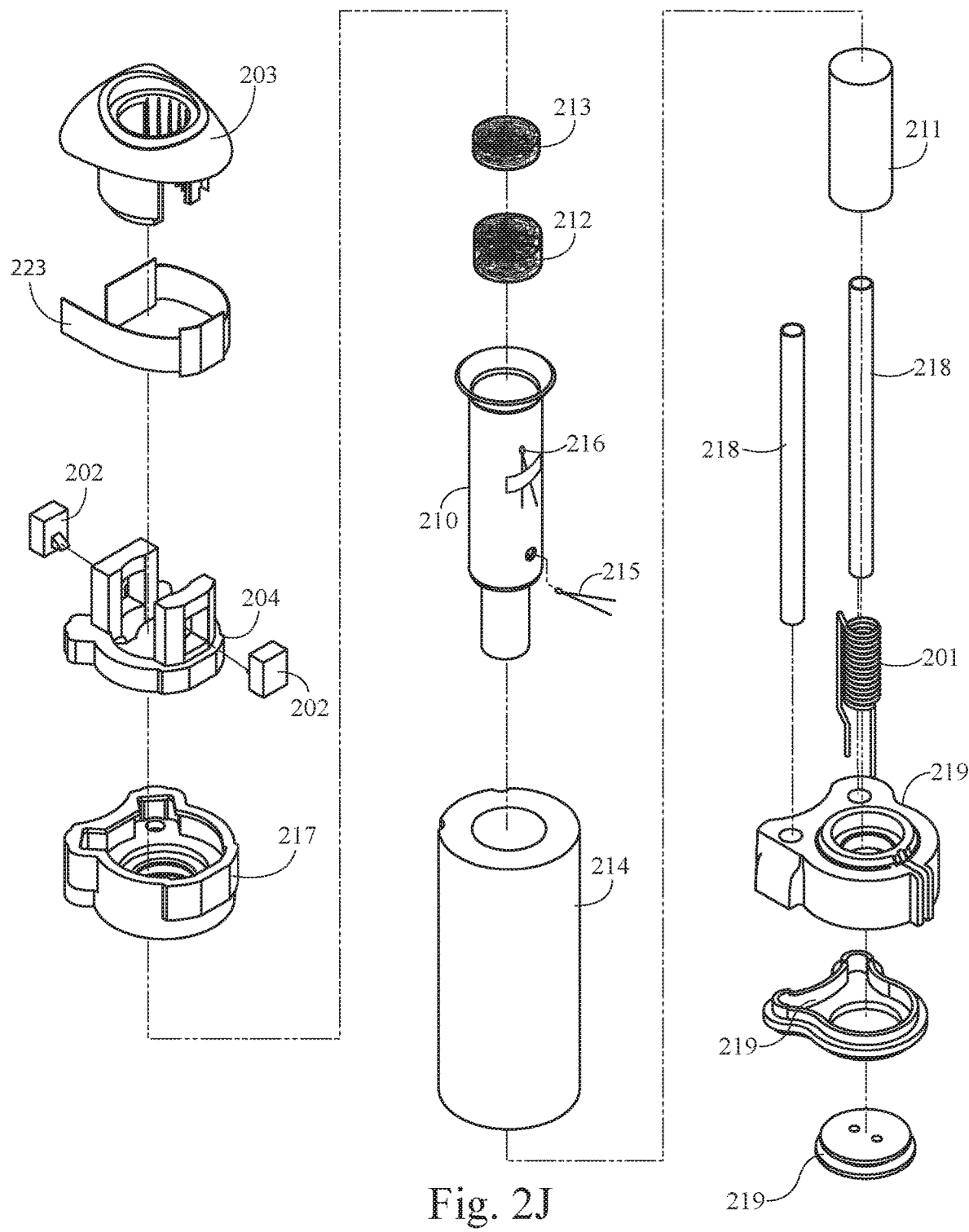
FIG. 2J is a detailed view of the first knitted wire filter.

FIG. 2J shows an exploded view of the major parts of the heating oven as they are arranged. In particular, oven tube 210 with at least two separate diameters and location of temperature sensors 215 and 216 are better shown.

Figure 3A:
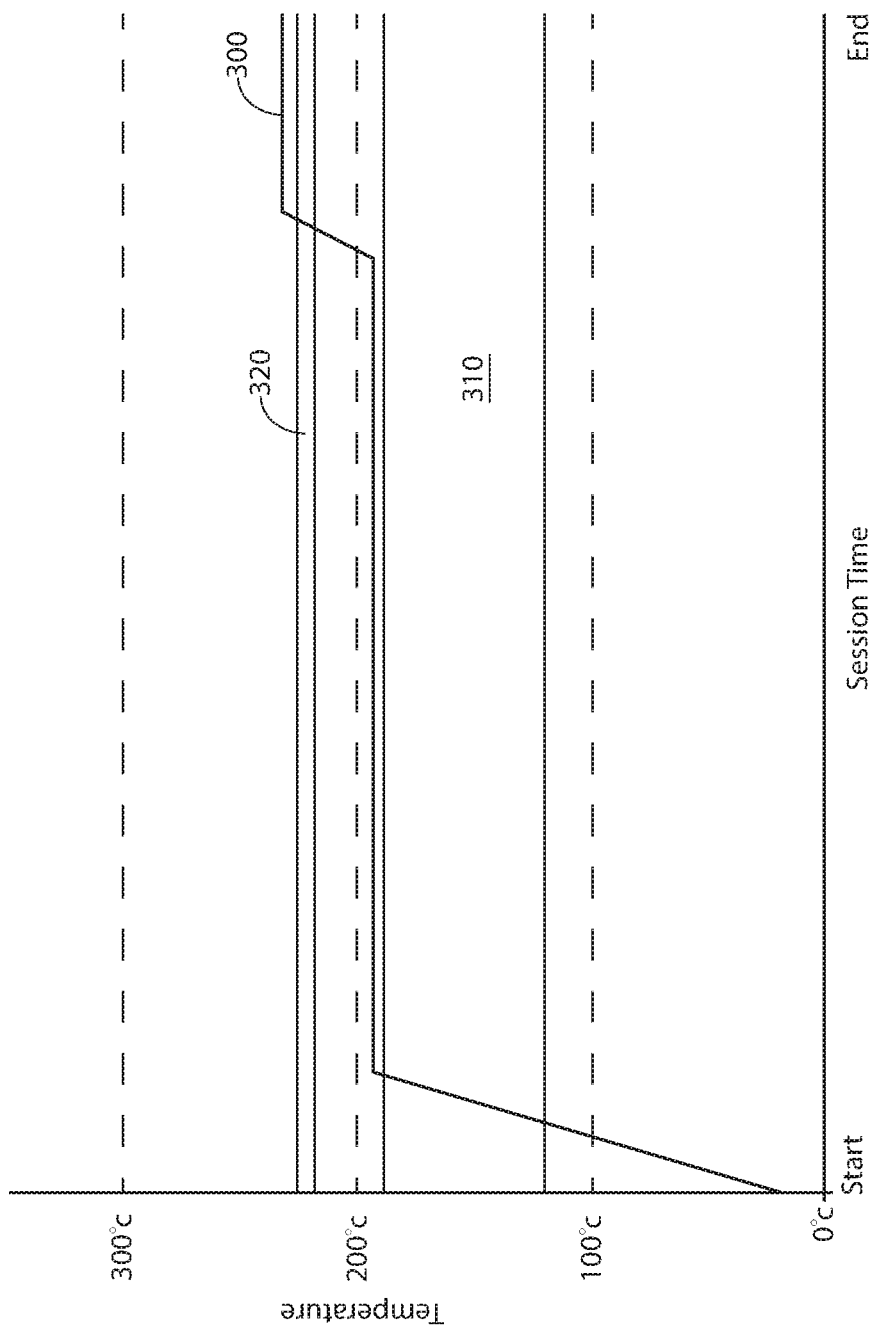
FIG. 3A is a chart showing an ideal temperature profile of the flower stick.

FIG. 3A is a chart that shows an ideal temperature profile of the flower stick. The ideal stick temperature curve 300 varies according to session time. Because different volatile compounds within the natural consumables vaporize at different temperatures, this variation allows for an optimal release of different classes of volatile compounds during the session.

A first class of compounds 310, or "Zone 1," may comprise terpenes in the form of b-caryophyllene, b-sitosterol, a-pinene, b-mycrene, limonine, cannaflavin, or linalool; and cannabinoids in the form of CBG, delta-9-THC, CBD, delta-8-THC, or CBN, with vaporization temperatures ranging from 120-185° C. A second class of compounds 320, or "Zone 2," may comprise terpenes in the form of terpineol-4-ol, a-terpineol, or pulegone; and cannabinoids in the form of CBC or THCV, with vaporization temperatures ranging from 200-220° C.

However, it is known that heating the stick beyond 200° C. results in smoking and charring of both the stick and contents. Heating the stick beyond 300° C. would cause combustion. Therefore, the oven would ideally be configured to quickly raise and maintain the temperature of the flower stick from ambient to between 185-200° C. This would be accomplished with an initial quick warmup of the oven from ambient to between 200-300° C. This allows for the quick release of Zone 1 compounds and evaporation of water within the natural consumables without the unpleasantness of experiencing smoking effects. This ideal heating profile also avoids the problem present in prior art heat-not-burn devices where the oven attains temperature gradually, which would result in a poor user experience in the form of slow warmup and cold mouth-feel.

Toward the end of the session, the oven quickly raises the temperature of the stick to above 220° C. This shorter portion of the session releases Zone 2 compounds, gives the experience of a "hot finish," while the relative shorter duration of high heat produces limited charring and smoking. At the end of the session, power to the heater coil is switched off, and the oven cools to ambient.

Figure 3B:
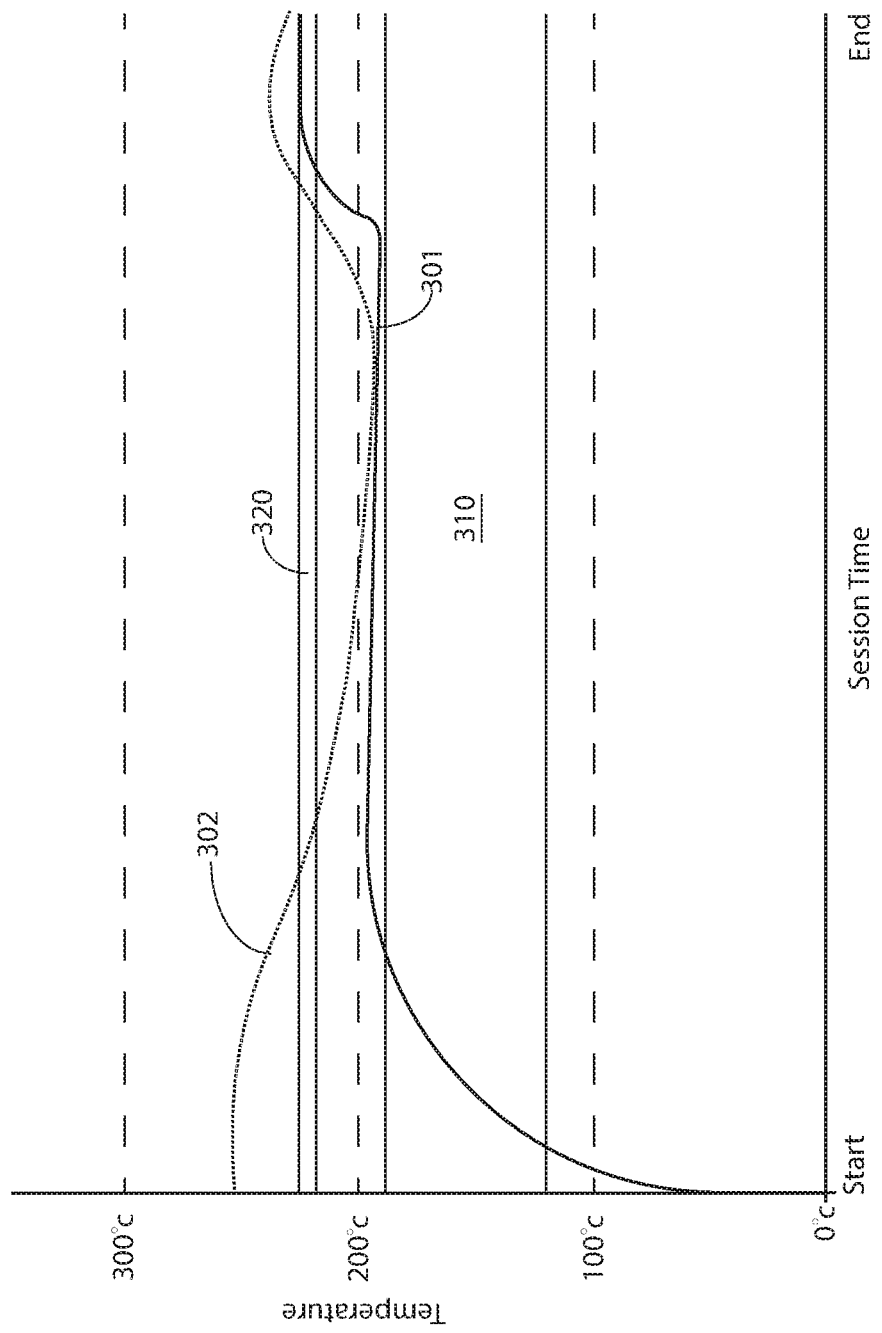
FIG. 3B is a chart showing temperature profiles of the oven and stick.

FIG. 3B shows the oven temperature curve 302 as it relates to the stick temperature curve 301. Initially, the oven quickly reaches a temperature between 200-300° C. and effectuate a rapid warmup of the stick. As the stick approaches its target temperature for vaporizing Zone 1 compounds and moisture is evaporated, oven temperature is reduced to keep the stick at the target temperature. Toward the end of the session, oven heat is again increased to raise the stick to its final temperature.

The temperature measured by the sensor at any time during the heating session, represented by the oven temperature curve 302, only roughly corresponds to the desired stick temperature curve 301 at any given time during the heating profile. This stick temperature has been measured during testing sessions, from which algorithms relating oven temperature to stick temperature have been derived, but the actual stick temperature cannot be precisely ascertained during actual user usage outside of a laboratory. Many factors, such as moisture content, active & volatile ingredients content, and packing density of the natural consumables, affect this relationship. For example, more energy is required to raise the temperature by a fixed amount at the start of the heating session, when the contents are more damp and most volatiles and active ingredients are still present, than later on during the session when the contents of the stick are drier and more of the active ingredients and volatile compounds have boiled off. Heating must be increased significantly when the user draws from the device and circulates a large amount of cool air through the oven in a short time. The oven temperature sensor(s) detect these fluctuations and is able to vary the amount of power into the device responsive to conditions.

Figure 3C:
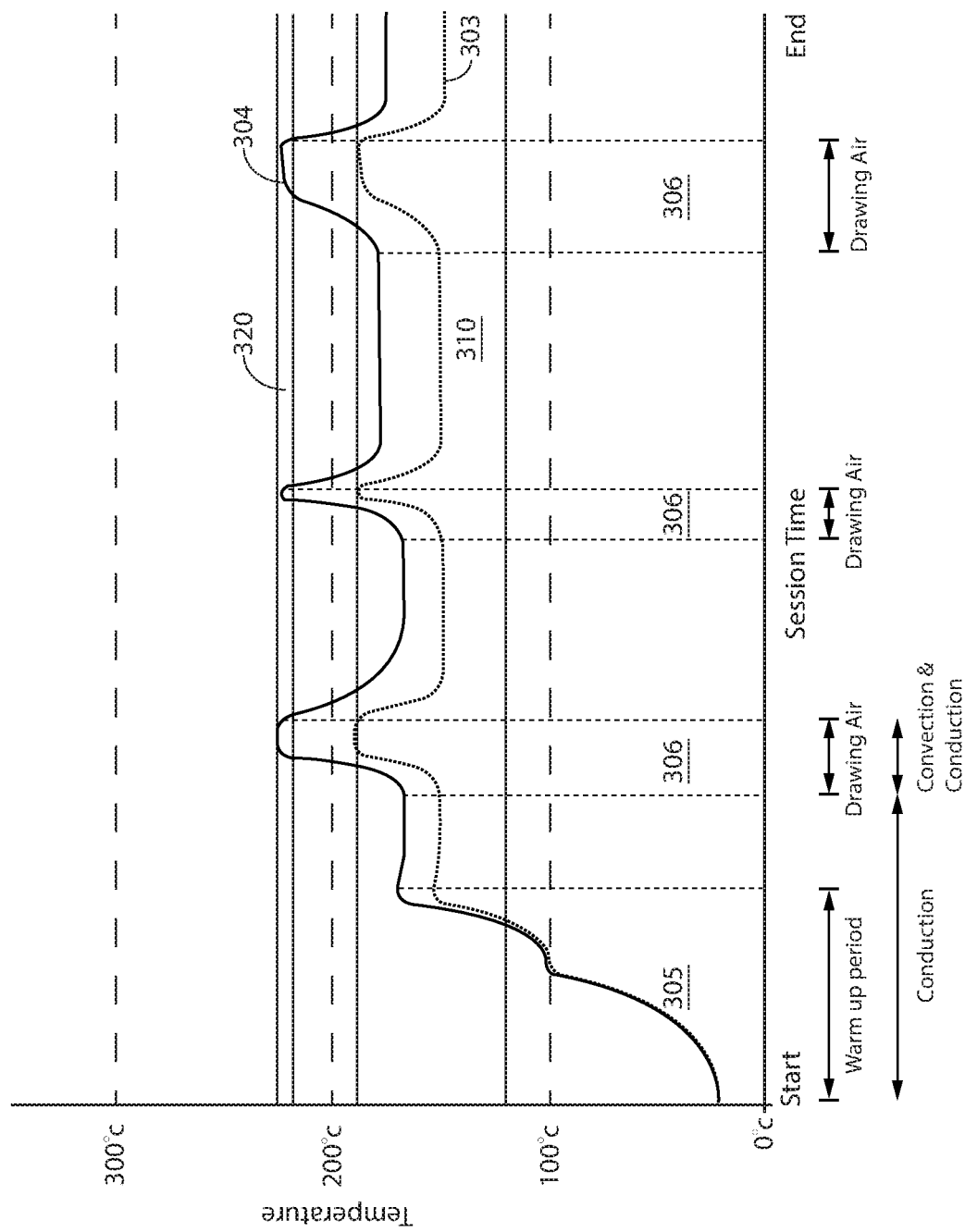
FIG. 3C is a chart showing additional embodiments of temperature profiles.

FIG. 3C illustrates two separate operating modes and desired methods to achieve additional temperature variability of the stick and natural consumables. Different types of natural consumables may necessitate a more appropriate temperature profile to provide a satisfactory user experience. The chart shows the resulting stick temperatures from two modes of operation, a first mode 303 operating at a lower temperature than a second mode 304.

In this embodiment, when extracting active ingredients from plant matter through vaporization it is desirable to ensure that the evaporation of active and volatile ingredients is minimized when the user is not drawing on the stick so that as much ingredients as possible are vaporized only at the moments when the user is drawing air through the stick. This reduces loss of the active ingredient and the premature drying and potential charring of the plant matter. It is therefore desirable to maintain the contents of the stick at a set temperature below the vaporization temperature of the desired active ingredients, and to raise the temperature rapidly, to a second predetermined temperature above the vaporization temperature of the desired ingredients for the period that the user is drawing on the device.

Initially both modes undergo a warm up period 305 where the stick temperature rises quickly from ambient to the initial target temperature via conduction only, since the user should have yet to inhale. Both modes will experience a slight pause in heating as the contents reach 100° C. to account for the latent heat of evaporating moisture. The warm up period concludes when the first mode reaches a temperature of 167° C. and the second mode reaches a resting temperature of 170-175° C. The stick is now primed for the user to draw from it.

As the user takes a drag 306, the oven must quickly increase the temperature to around 190° C. for the first mode and 220° C. for the second mode to release the full spectrum of the desired compounds. This is accomplished, during drawing, by both convection and conduction. As the user finishes inhaling, the power is reduced and the temperature of the stick allowed to fall back to the target resting temperature. This continues throughout the session as multiple drags are taken, each with varying duration and inhalation speed, as contemplated by the shape of the curves. The oven attempts to minimize the time that it is in the "hot" zone when the user is not drawing.

These short periods in which the stick temperature is quickly raised and then lowered minimizes the part of the curve where the stick exceeds 200° C. and causes the unpleasant experience of burning and "smoking" in the form of particulate emission. It is also contemplated that both modes may gradually increase the target temperature depending on the elapsed time for the "hot finish" illustrated in FIGS. 3A and 3B.

The advantages of the dual convection-conduction oven are apparent in the present invention. A vaporizer utilizing only conduction draws cool air into the oven when the user draws, cooling the contents and giving a reduced output and disappointing "cold" experience on voluminous draws. A vaporizer utilizing only convection, on the other hand, need to raise the temperature on each draw by such a significant amount that some parts of the stick may reach or exceed charring temperatures before the natural consumables farthest from the heat source are activated. Using both convection and conduction allows the vaporizer to maintain the contents at an optimal temperature between user draws, and preserves flexibility when air is actively circulated.

Additional features, notably the use of the knitted wire filters with the properties of high surface area, high thermal mass, high thermal conductivity, and particular construction aspects of the knitted wire filters themselves, that controlled heating of the flower stick can be achieved.

Temperature regulation of the oven is enabled via signaling collected by the temperature sensors. Variable power to the heater coil is applied via frequency-modulated signals that range between 0 and 44 watts. The pulse-width modulation (PWM) is applied at not less than 10,000 Hz to avoid buzzing due to rapid expansion and contraction of the coil. Based on the capabilities of the control circuitry, it is estimated that temperature variation from the ideal temperature profile is not more than 20° C. at any given time during the session.

The coil has a resistance of ~0.4 ohms and the battery delivers a nominal voltage of 3.7-4.2V giving a potential current of 10.5 Amps and a maximum power of ~44 Watts as applied to the oven. In actual use, the power to the coil is pulse-width modulated (PWM) such that the power delivered to the coil is proportional to the difference between the actual temperature measured by the sensor and the desired optimal temperature at that time within the heating session.

All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A dual conduction-convection heating oven for use with a portable electronic heating device for delivery of vaporized consumables within a flower stick, the oven comprising:
  a heating coil that produces heat by electrical current;
  an oven tube adapted to transfer heat produced by the coil to the flower stick via conduction;

one or more knitted wire filters adapted to absorb heat produced by the coil.

2. The oven of claim 1, wherein the oven tube is configured to heat-exchange with a flower stick by means of conduction.

3. The oven of claim 1, wherein the one or more knitted wire filters are configured to heat-exchange with air flowing through the filters.

4. The oven of claim 1, wherein a first knitted wire filter comprises wires of aluminum, brass, or copper.

5. The oven of claim 4, wherein a second knitted wire filter comprises wires of stainless steel.

6. The oven of claim 1, wherein the one or more knitted wire filters are compressed into a cylindrical shape.

7. The oven of claim 1, wherein the one or more knitted wire filters are configured with a notch or indentation adapted to fit one or more sensors and signal wires.

8. The oven of claim 1, wherein the one or more knitted wire filters are adapted to heat-exchange with air flowing through the filters to a higher temperature than the temperature of the oven tube in contact with a flower stick.

9. The oven of claim 1, further comprising one or more stick switches triggered by the insertion of the flower stick into the heating oven, or removal of the flower stick from the heating oven.

10. The oven of claim 1, further comprising an oven top gasket configured to form an airtight seal with the flower stick at a location above an open end of the oven tube.

11. The oven of claim 1, further comprising one or more temperature sensors.

12. The oven of claim 11, wherein a first temperature sensor is positioned within a knitted wire filter.

13. The oven of claim 12, wherein a second temperature sensor is positioned between two knitted wire filters.

14. The oven of claim 1, wherein the oven tube further comprises a segment of smaller diameter adapted to absorb heat energy from the heating coil, and a segment of larger diameter adapted to receive the flower stick inserted into the oven tube.

15. The oven of claim 1, wherein the knitted wire filters are thermal masses adapted to retain heat and regulate airflow temperature.

16. A dual conduction-convection heating oven for use with a portable electronic heating device for delivery of vaporized consumables within a flower stick, the oven comprising:
   a heating coil that produces heat by electrical current;
   an oven tube adapted to transfer heat produced by the coil to the flower stick via conduction;
   one or more knitted wire filters adapted to absorb heat produced by the coil;
   a stick guide;
   one or more air tubes;
   a base assembly;
   wherein airflow traverses the stick guide, one or more air tubes, and base assembly through preformed channels before entering the heating coil.

17. The oven of claim 16, wherein the one or more knitted wire filters are configured to heat-exchange with air flowing through the filters.

18. The oven of claim 16, wherein the one or more knitted wire filters are adapted to heat-exchange with air flowing through the filters to a higher temperature than the temperature of the oven tube in contact with a flower stick.

19. The oven of claim 16, further comprising an oven top gasket configured to form an airtight seal with the flower stick at a location above an open end of the oven tube.

20. The oven of claim 16, wherein the oven tube further comprises a segment of smaller diameter adapted to absorb heat energy from the heating coil, and a segment of larger diameter adapted to receive the flower stick inserted into the oven tube.

* * * * *